United States Patent [19]

Lake

[11] 4,095,295

[45] Jun. 20, 1978

[54] ADJUSTABLE, FLUID-FILLED BREAST IMPLANT

[76] Inventor: Douglas Lake, 21 Elsway Rd., Short Hills, N.J. 07078

[21] Appl. No.: 781,734

[22] Filed: Mar. 28, 1977

[51] Int. Cl.² ............................ A61F 1/24; A41C 3/10
[52] U.S. Cl. ................................................... 3/36
[58] Field of Search ........................ 3/36, 1; 128/462

[56] References Cited

U.S. PATENT DOCUMENTS

| | | | |
|---|---|---|---|
| 3,416,160 | 12/1968 | Arion | 3/36 |
| 3,461,869 | 8/1969 | Hargest | 3/1 X |
| 3,665,520 | 5/1972 | Perras et al. | 3/36 |
| 3,831,583 | 8/1974 | Edmunds, Jr. et al. | 3/1 X |
| 3,852,832 | 10/1974 | McGhan et al. | 3/36 |
| 3,860,969 | 1/1975 | Arion | 3/36 |
| 3,883,902 | 5/1975 | Lynch | 3/36 |
| 3,919,724 | 11/1975 | Sanders et al. | 3/36 |

*Primary Examiner*—Ronald L. Frinks
*Attorney, Agent, or Firm*—Martha G. Pugh

[57] ABSTRACT

An improved fluid-filled breast prosthesis for implantation which permits subsequent alterations in the fluid volume of the implant without the necessity for major surgery. The prosthesis comprises a flexible plastic bag having an elongated filler tube including a loop near its outer end. After the prosthesis has been interposed into the surgically prepared implant site, the filler tube is drawn out through a small stab wound connected to the site which terminates adjacent the arm pit. After the plastic bag is filled with fluid, the filler tube is plugged and clamped, and the loop is sutured to the tissue to hold the implant in place. The radiopaque nature of the plug and clamp, and a connected filament, enable the end of the tube to be readily located and grasped subsequent to the operation, using a simple office procedure to adjust the volume of fluid in the bag.

14 Claims, 10 Drawing Figures

ADJUSTABLE, FLUID-FILLED BREAST IMPLANT

BACKGROUND OF THE INVENTION

This relates, in general, to prosthetic devices for surgical implantation; and, more particularly, to improvements in devices and techniques employing breast implants comprising fluid inflatable bodies.

The inventor practices plastic surgery and it has been his observation that one of the most common complaints of patients who have had breast implants for cosmetic reasons is hardness of the implants, producing an unnatural, firm feeling of the breast; and that such harness may be due, at least in part, to the formation of a tight fibrous capsule around the implant, producing a squeezing constricting effect and causing firmness by this pressure on the contents of the implant. However, this fibrous reaction terminates after one or two months when the tissue reaction ceases and the size of the fibrous sac around the implant becomes stabilized without further shrinkage. One of the principal causes of this reaction is the postoperative formation of hematoma around the implant due to postoperative bleeding. If some of the contents of the implant are withdrawn at any time after the fibrous tissue reaction ceases, the implant will become soft and will remain so indefinitely. It is usually only necessary to remove a small part of the contents of the implant, 25-50 cc. of a total volume of 200-350 cc., to produce the desired effect of softening the implant to simulate the softness of normal breast tissue.

Another common problem is that patients who undergo implantation of silicone breast prostheses for cosmetic reasons often decide that they wish to have the breast made smaller or larger than the originally agreed size, at some later date. Both of these complications of breast surgery can be corrected by altering the volume of the fluid, saline or water, in the implant to satisfy the patient's requirements. However, such an alteration involves all of the discomfort, hazard and expense of the original operation and, since it creates a presumption that the original operation may not have been properly performed, creates an additional hazard of malpractice litigation.

Means is provided in connection with certain types of prior art prosthetic devices comprising flexible containers, such as disclosed, for example, in U.S. Pat. Nos. 3,600,718 to J. L. Boone, 3,852,832 to McGhan et al, 3,883,902 to H. W. Lynch and 3,919,724 to Sanders et al, for filling the device up to a desired volume of fluid, and then sealing it. However, in the devices mentioned, once the filling operation has been completed, the filler tube is no longer conveniently available for a subsequent operation to adjust the fluid volume, as the length of the filler tube has either been removed altogether, cut off and sealed at a short length, or directed internally into the prosthesis. Moreover, the insert valves for the filling procedure are either completely inaccessible without major surgery, or they are positioned in a disfiguring manner on the front portion of the prosthesis. In either case, the sealed end of the filler tube makes an additional lump in the prosthesis which may be unsightly or hard to the touch.

Another disadvantage realized in many of the breast implantation prostheses of the prior art types is that unless they are securely anchored to the tissues by complicated surgical procedures, such as described, for example, by McGhan et al, they tend to move about on the implantation site. This may give discomfort to the wearer, and raises additional problems if it is desired to locate the intake valve for subsequently adjusting the volume of fluid in the container.

SUMMARY OF THE INVENTION

Accordingly, it is the general object of the present invention to provide improvements in breast implants comprising fluid inflatable bodies. A more particular object of the invention is to facilitate adjustment of the volume of fluid in the implant subsequent to surgical implantation. A further object of the invention is to provide means for permanently anchoring the implant.

In accordance with the present invention, these and other objects are attained by a fluid inflatable breast prosthesis comprising a valveless bag having an elongated filler tube equipped near its external end with a loop for suturing, means for closing off the tube; and the techniques for implantation of the prosthesis.

The site for the implant is prepared by making a semicircular incision around the lower periphery of the areola. The breast tissue is then elevated from the pectoral facia and muscle to create a pocket for the implant, which pocket is extended to the axillary crease just behind the anterior axillary fold. A small stab wound is made horizontally in the crease behind the anterior axillary fold, which connects with the extension of the pocket.

The bag comprising the breast prosthesis, which is preferably of silicone rubber or some other nontoxic flexible plastic, including an elongated filler tube of flexible plastic having a loop for suturing, is introduced empty into the implant site through the areolar incision. The attending surgeon reaches through the stab wound into the pocket to grasp the filler tube, which is drawn through the stab wound until it protrudes adjacent the arm pit. The empty bag is thus positioned and secured in the implant site.

The areolar incision is then surgically closed, after which the implant bag is inflated with fluid to the desired volume. The inflating fluid for this purpose is preferably a normal saline solution, or distilled water, although other physiologically compatible fillers may be used. When the filling operation is completed, a cylindrical plug is placed in the end of the tube, and the neck of the tube is clamped beyond the plug with a small clip. The plug includes a radiopaque filament which is disposed to hang from the end of the tube about 1 inch in length, to permit grasping with forceps for withdrawal of the plug. The loop near the end of the filler tube is sutured to tissue prior to the suturing of the stab wound.

The device and techniques described above provide the following advantages over the prior art. The filler tube, together with the radiopaque filament, is readily accessible for readjusting the volume of fluid in the implant bag without the necessity for additional major surgery. The tube, together with the suturing loop, provides means for anchoring the prosthesis in place during the healing period. Valves and other filling devices are avoided, which may leak or create undesirable lumps in the breast, as well as active, concurrent and postoperative aspiration to eliminate hematoma formation which is the principal cause of fibrosis and hardening of breast implants.

These and other objects, features and advantages will be apparent from a study of the specification hereinafter with reference to the attached drawings.

DETAILED DESCRIPTION

Figure 1:
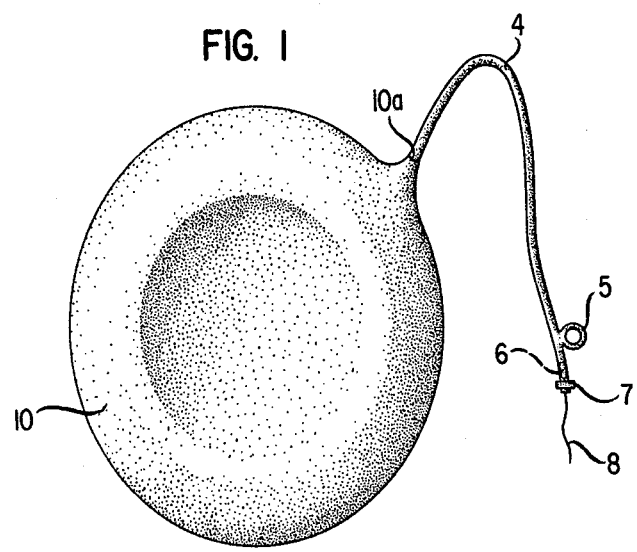
FIG. 1 shows a diagram of a breast prosthesis in accordance with the present invention, including an elongated filler tube and a loop for suture.

Referring to FIG. 1, there is shown a breast prosthesis comprising a valveless bag 10 composed of any nontoxic flexible plastic material impermeable to liquid, which is known in the art, such as, for example, a medical grade of silicon elastomer sold under the name of General Electric Elastomeric Resin 7000. The latter contains $R_2SiO_4$ groups, and small amounts of vinyl $R_2SiO$, where R represents methyl groups. This elastomer is known to have characteristics such as softness and resiliency which may be made to approximate those of the human body. A silicone membrane useful for the purpose of the present invention is preferably characterized by osmotic properties which essentially follow Fick's Laws of Diffusion, as defined, for example, in the article entitled "Diffusion in gases and liquids, Molecular diffusion", pages 154–155, Volume 4, McGraw-Hill Encyclopedia of Science and Technology, Copyright McGraw-Hill 1971. Oxygen, hydrogen and materials in a nonionized state permeate through the membrane so that small air bubbles trapped in the prosthesis when filled, pass through in a short time. Another product useful for the purposes of the present invention in an organo siloxane copolymer of the type set forth in U.S. Pat. No. 3,665,520 to Perras et al.

The bag 10, when deflated, is pancake-shaped, say, 4 inches in diameter, and when inflated assumes the shape of the human breast. When formed of silicone elastomer, it has a wall thickness of, say, 0.012–0.20 inch (0.3 to 0.5 mm.), and weighs from 8 to 16 grams. At one point on the periphery of bag 10 is a collar 10a into which is integrally welded a tube 4, formed of any soft flexible pliable plastic material, impervious to liquid, such as, for example, one of the materials described in the preceding paragraph. In the present embodiment, the tube 4 is approximately ⅛ inch in outer diameter and 3/32 inch in inner diameter and at least about 4 inches long, extending in a radial direction from the periphery of the bag 10. Formed about ½ inch in from the outer tip of tube 4 is a loop 5 which is 1/16 inch in inner diameter and ⅛ inch in outer diameter. Radiopaque plug 6, with attached filament 8, and clip 7, both supplied with the prosthesis, are used to close off the tube in a manner to be subsequently described.

Figure 2A:
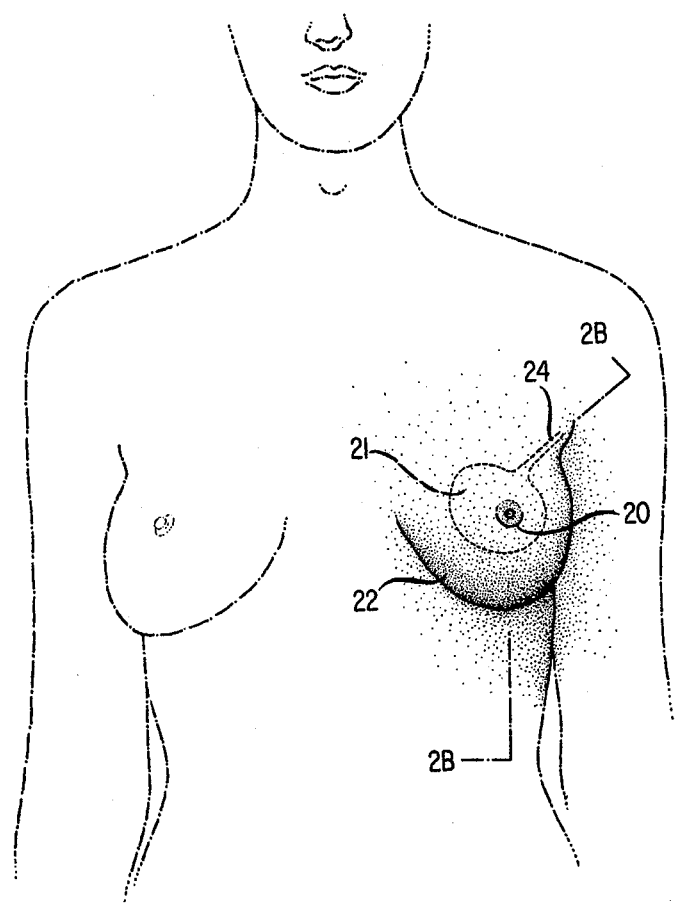
FIG. 2A is a front view of the upper female torso with the implant site surgically prepared on the left-hand breast.
Figure 2B:
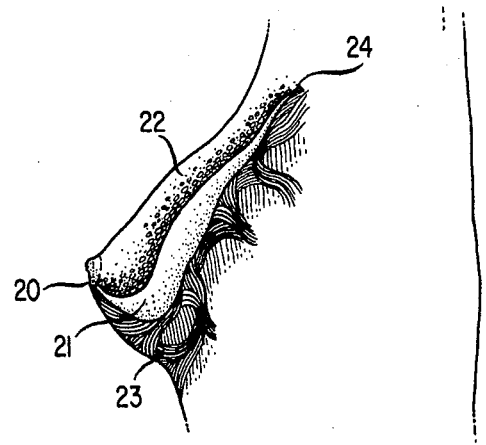
FIG. 2B is a section through the plane 2B—2B of FIG. 2A showing the surgically prepared implant site.

Referring to FIG. 2A, which is a frontal view of the upper female torso, assuming the left-hand breast is being operated on, a semicircular incision, just within the lower periphery of the areola, is first made by the surgeon moving the scalpel in a clockwise direction from a position corresponding to three o'clock to a position corresponding to nine o'clock. In accordance with procedures well-known in the art, the breast tissue 22 is elevated, and a pocket 21 is created between the breast tissue and the pectoralis major muscle 23, as shown in section in FIG. 2B of the drawings. The pocket is extended surgically to the axillary crease just behind the anterior axillary fold, as shown in FIGS. 2A, 2B. As a particular feature of the present invention, a short stab wound incision 24 is made in the axilla, just behind the anterior axillary fold, and carried down through the subcutaneous fat to connect with the surgical pocket 21.

Figure 3A:
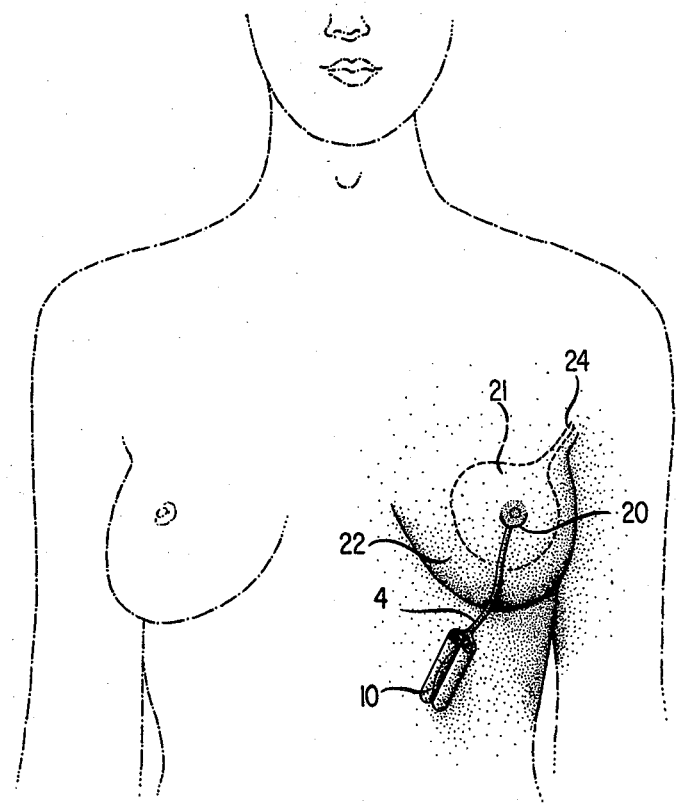
FIG. 3A shows the collapsed implant in the process of being interposed through the incision into the surgically prepared site during the operational procedure.
Figure 3B:
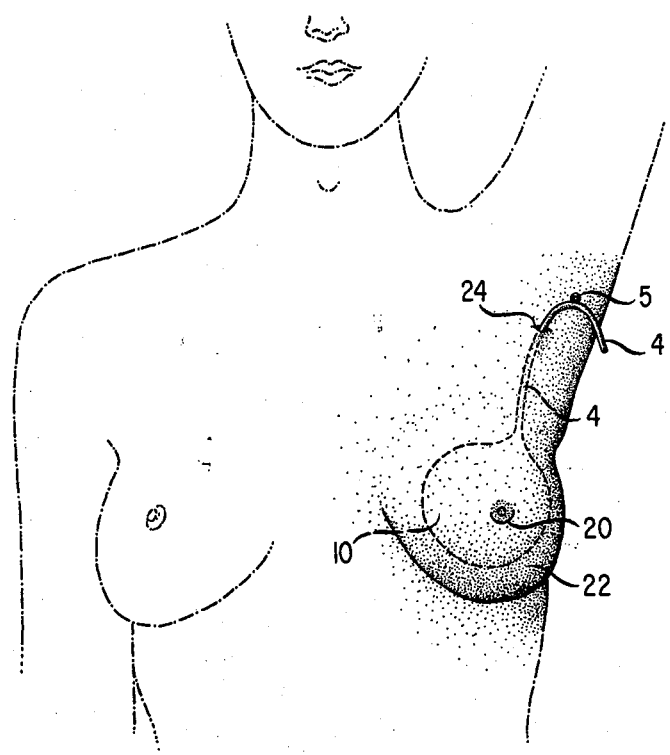
FIG. 3B shows the outline of the collapsed implant in place in the surgically prepared site, with the filler tube extending out through the stab wound behind the anterior axillary fold.

The flexible plastic implant bag 10, including the filler tube 4, which has been properly sterilized, is interposed empty into the surgical pocket 21, through the areolar incision 20, in the manner shown in FIG. 3A. The tube 4 is then grasped by forceps and drawn out through stab wound 24, positioning the bag 10 in place in the pocket 21, as shown by the dotted lines in FIG. 3B.

Figure 4:
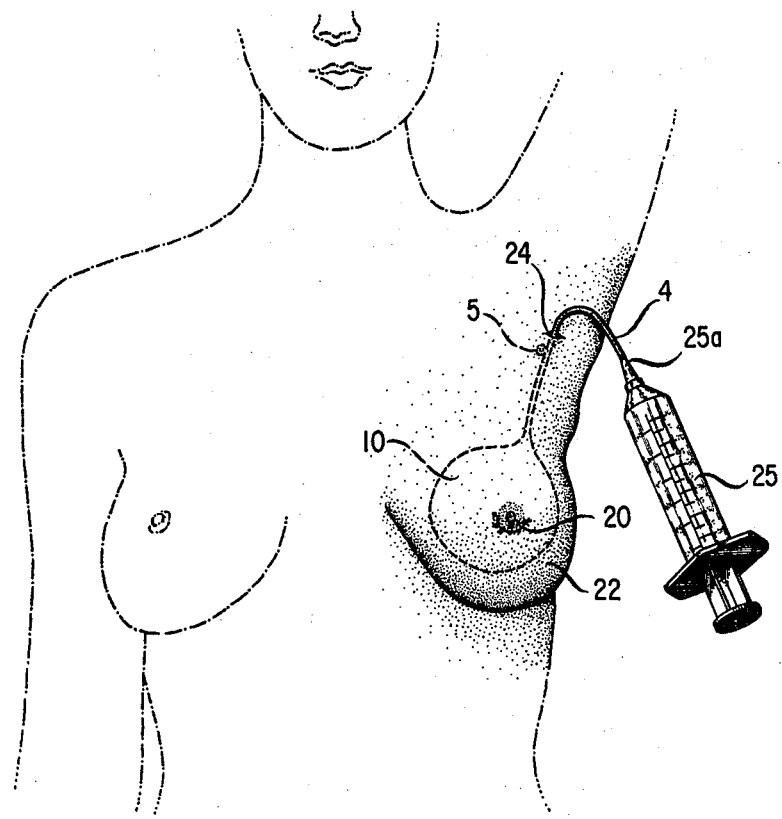
FIG. 4 shows the aerolar incision sutured closed, and a hypodermic needle connected to the filler tube for pumping the implant full of saline solution.

The areolar incision 20 is then sutured closed, as indicated in FIG. 4. After completion of this step, the implant bag 10 is filled to the desired volume in a manner well-known in the art, by pumping anywhere from about 150 to 350 cc. of fluid through the filler tube 4. For this purpose, a conventional type of hypodermic needle 25, which has been filled in advance with the required fluid, is connected through a conventional adapter 25a to the free end of tube 4, in the manner indicated in FIG. 4.

A preferred fluid for the purposes of the present invention is a normal saline solution, designated N/saline, which consists of 0.9 percent NaCl dissolved in water. It will be understood, however, that many other types of liquids may be used for the purposes of the present invention, the principal requirement being that the solution is nontoxic, does not substantially react with the body fluids and has a relatively low viscosity so that it can be pumped freely into the bag 10 through the small diameter tube 4 without drying up or crystallizing so as to stop up the tube.

After the bag 10 has been filled to the desired volume, the hypodermic 25 and adapter 25a are removed from the end of tube 4.

Prior to suturing, a disposable aspiration tube is placed into the surgical pocket 21 through the stab wound 24, being left for about a day for draining the wound of any accumulated blood clots or other secretions. Before the wound 24 is sutured, the tube 4 must be plugged, clamped and sutured in place.

Figure 5:
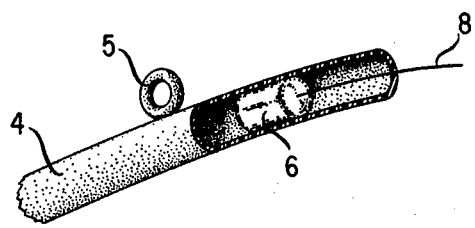
FIG. 5 is an enlarged showing of a plug interposed into the end of the filler tube.

Part of the kit of the breast prosthesis 10 includes an occluding plug 6 and a surgical clip 7. The plug 6 is a radiopaque cylinder with rounded ends, say, 3/16 to ¼ inch long and 3/32 inch in diameter, which is formed of a nontoxic radiopaque, semirigid plastic material. This is interposed into the end of the tube 4 about one-half to 1 inch from the end, as shown in FIG. 5. In a preferred embodiment, a thread or filament 8 of cotton or any non-toxic radiopaque material, say, 1 or 2 inches long, and of sufficient tensile strength to permit withdrawal of the plug, is molded into the body of plug 6, so that it extends along its principal axis and hangs out the end of tube 4. The clip 7 is a conventional v-shaped surgical clamp, preferably of Vitallium, strong enough to hold the end of tube 4 closed. In the present embodiment, the legs of the clip 7 are 0.276 inch (7 mm.) long and 0.079 to 0.118 inch (2 to 3 mm.) wide. Clip 7 is applied near the end of tube 4, as shown in FIG. 6.

Figure 7A:
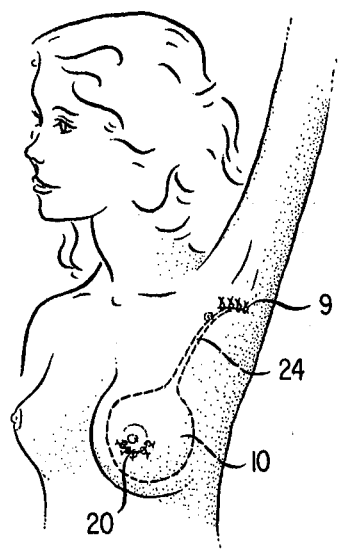
FIG. 7A is a lateral perspective view of the patient showing the stab wound sutured.
Figure 7B:
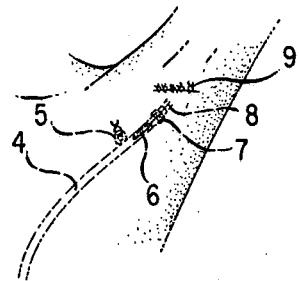
FIG. 7B is an enlarged showing of the sutured stab wound, indicating the positions of the occluding plug, clip and sutured loop adjacent the end of the filler tube.
Figure 6:
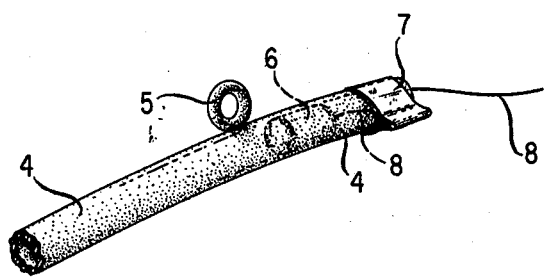
FIG. 6 is an enlarged showing of a clip disposed to close off the end of the filler tube.

After the plug 6 and clip 7 are in place, the loop 5, shown in FIGS. 5 and 6, is sutured to subcutaneous tissue just below stab wound 24 with nonabsorbable suture; and the stab wound 24 is then closed to form a suture 9, as shown in FIG. 7A. FIG. 7B is a detailed showing of the position of the end of tube 4, including the loop 5, radiopaque plug 6, clip 7 and cord 8, after stab wound 24 has been closed.

At a later date, if the patient complains of hardness of the implant, or for any other reason, the arterial clip 7 can be located both by X-ray and palpation, and its location accurately determined. A small stab wound incision will locate the tip of the implant tube 4 and the arterial clip 7. The tube 4 can be opened, the volume of fluid in the implant 10 adjusted to the desired quantity, and the tube 4 resealed and the new stab wound closed. Since the tip of the tube 4 would be widely separated from the body of the implant 10, and the tissues healed around it, the hazard, discomfort and expense of a breast reoperation would be eliminated. The procedure of volume adjustment of the implant 10 can be repeated as often as required as a minor office procedure, without risk or discomfort to the patient. Further, suturing of the loop 5 of filling tube 4 of the implant to the tissues in the axilla tends to fix the implant 10 in place to prevent undesirable rotation within the sack, and sagging of the sack.

It will be understood that the present invention is not limited to the specific form or materials of the disclosed illustrative embodiment, or the procedural steps set forth by way of illustration, but only by the scope of the appended claims.

What is claimed is:

1. A mammary prosthetic implant comprising in combination:
   a liquid inflatable valveless bag of liquid impervious flexible material,
   a filler tube of flexible liquid impervious material integral with an opening in the periphery of said bag and extending outward therefrom,
   means for suturing said filler tube to tissue comprising a loop formed integrally with said tube near its external end.

2. The combination in accordance with claim 1 including means for occluding said tube which facilitates reopening, comprising a plug constructed and arranged to be fitted into the external end of said tube.

3. The combination in accordance with claim 2 wherein said occluding means includes a surgical clip constructed to close the end of said tube.

4. The combination in accordance with claim 3 wherein said clip is of radiopaque material, and said plug is of a semi-rigid nontoxic radiopaque plastic material.

5. The combination in accordance with claim 4 wherein a filament of radiopaque material is connected to said plug and is disposed to extend out from the external end of said tube when said plug is fitted therein.

6. The combination in accordance with claim 1 wherein the materials of said bag and of said filler tube are characterized by a softness and resiliency approximating those of the human body, which essentially follow Fick's laws of diffusion, and said tube isat least about 4 inches long as measured from the periphery of the bag.

7. The combination in accordance with claim 6 wherein said bag and said filler tube are formed essentially of silicone elastomer.

8. The combination in accordance with claim 6 wherein said bag and said filler tube are formed essentially of an organo siloxane copolymer.

9. The method of implanting a liquid inflatable mammary prosthesis which comprises the steps of:
   surgically preparing the implantation site by making a semicircular incision below the lower periphery of the areola,
   forming a pocket to accommodate the prosthesis between the breast tissue and the pectoralis major muscle,
   surgically extending said pocket to the anterior axillary crease,
   making a stab wound in the axilla which connects to said pocket,
   interposing into said pocket through said areolar incision a mammary prosthesis in the form of an empty bag of flexible liquid impervious material having an elongated filler tube,
   drawing said filler tube through said stab wound so that the end of said tube protrudes from said axilla,
   suturing closed said areolar incision,
   connecting said filler tube to a liquid source for pumping liquid into said bag to a desired volume,
   occluding said filler tube by interposing a plug near the external end of said tube,
   securing said filler tube to the patient's tissue adjacent the anterior axilla, and
   suturing said stab wound closed.

10. The method in accordance with claim 9 wherein said plug is a semirigid radiopaque nontoxic plastic material.

11. The method in accordance with claim 10 wherein the end of said tube is closed with a radiopaque surgical clip.

12. The method in accordance with claim 11 wherein a radiopaque filament is attached to said plug, and is disposed to extend out from the end of said tube and remain so extended after the suturing of said stab wound.

13. The method in accordance with claim 9 wherein said filler tube is formed to include a loop integral therewith adjacent the external end, and
   said filler tube is secured to the patient's tissue by suturing said loop to the patient's tissue.

14. The method of adjusting the volume of liquid in a liquid inflatable mammary prosthesis implanted in accordance with claim 12, subsequent to implantation, which comprises the steps of:
   using an X-ray probe to locate the site of any one of the radiopaque clip, plug or filament,
   making a small stab wound at the said site,
   grasping the said filament to remove the occluding plug from the said filler tube,
   connecting said filler tube to a liquid source for adjusting the liquid in said bag to a desired volume,
   removing said source of liquid, replacing said plug and suturing said stab wound.

* * * * *

UNITED STATES PATENT AND TRADEMARK OFFICE
CERTIFICATE OF CORRECTION

PATENT NO. : 4,095,295
DATED : June 20, 1978
INVENTOR(S) : Douglas Lake

It is certified that error appears in the above-identified patent and that said Letters Patent are hereby corrected as shown below:

Column 1, line 14 - change "harness" to --hardness--.

Column 3, line 53 - change "in" to --is--.

Claim 6, line 5 - change "isat" to --is at--.

Signed and Sealed this

Twentieth Day of March 1979

[SEAL]

Attest:

RUTH C. MASON
Attesting Officer

DONALD W. BANNER
Commissioner of Patents and Trademarks